United States Patent
Begg et al.

(10) Patent No.: US 11,805,998 B2
(45) Date of Patent: Nov. 7, 2023

(54) DEVICES AND METHODS FOR OBTAINING ADENOMYOSIS AND OTHER BIOPSY SAMPLES

(71) Applicant: Covidien LP, Mansfield, MA (US)

(72) Inventors: Nikolai D. Begg, Wellesley, MA (US); Chad A. Pickering, Woburn, MA (US); Dalia P. Leibowitz, Cambridge, MA (US); Timothy J. Wood, Wilmington, MA (US); Andrew P. Bolognese, Waltham, MA (US)

(73) Assignee: Covidien LP, Mansfield, MA (US)

( * ) Notice: Subject to any disclaimer, the term of this patent is extended or adjusted under 35 U.S.C. 154(b) by 695 days.

(21) Appl. No.: 16/853,016

(22) Filed: Apr. 20, 2020

(65) Prior Publication Data
US 2021/0321993 A1   Oct. 21, 2021

(51) Int. Cl.
A61B 10/02 (2006.01)
A61B 10/04 (2006.01)

(52) U.S. Cl.
CPC .......... *A61B 10/0291* (2013.01); *A61B 10/04* (2013.01)

(58) Field of Classification Search
CPC .......... A61B 10/04; A61B 2010/0216; A61M 2025/0004; A61M 2025/1065; A61M 25/1006; A61M 2025/1086
See application file for complete search history.

(56) References Cited

U.S. PATENT DOCUMENTS

| | | | |
|---|---|---|---|
| 2,426,535 A | 8/1947 | Turkel | |
| 3,513,830 A | 5/1970 | Kalayjian | |
| 3,683,892 A | 8/1972 | Harris | |
| 4,306,570 A * | 12/1981 | Matthews | A61B 10/025 600/568 |
| 4,651,752 A | 3/1987 | Fuerst | |
| 5,183,052 A | 2/1993 | Terwilliger | |
| 5,188,118 A | 2/1993 | Terwilliger | |
| 5,195,533 A | 3/1993 | Chin et al. | |
| 5,249,583 A * | 10/1993 | Mallaby | A61B 10/0275 600/568 |
| 5,250,059 A | 10/1993 | Andreas et al. | |
| 5,251,641 A | 10/1993 | Xavier | |
| 5,526,822 A | 6/1996 | Burbank et al. | |
| 5,538,010 A | 7/1996 | Darr et al. | |
| 5,718,237 A | 2/1998 | Haaga | |
| 5,827,305 A | 10/1998 | Gordon | |
| 5,944,716 A | 8/1999 | Hektner | |
| 6,010,522 A | 1/2000 | Barbut et al. | |
| 6,272,372 B1 | 8/2001 | Fisher | |
| 6,296,639 B1 | 10/2001 | Truckai et al. | |

(Continued)

*Primary Examiner* — Rene T Towa
(74) *Attorney, Agent, or Firm* — Carter, DeLuca & Farrell LLP (57) ABSTRACT

A tissue biopsy device includes an input configured to receive a rotational input and to rotate in a first direction in response thereto, an outer tube, and an inner cutting member extending through the outer tube. A mechanism couples the input with at least one of the inner tube or the outer tube and/or one of the inner tube or the outer tube is coupled to the input such that rotation of the input in the first direction drives rotation of the one of the outer tube or the inner cutting member in the first direction and drives rotation of the other of the outer tube or the inner cutting member in a second, opposite direction.

14 Claims, 5 Drawing Sheets

(56) References Cited

U.S. PATENT DOCUMENTS

| | | | |
|---|---|---|---|
| 6,402,701 B1 * | 6/2002 | Kaplan | A61B 10/0233 |
| | | | 600/567 |
| 6,659,105 B2 | 12/2003 | Burbank et al. | |
| 6,730,045 B2 | 5/2004 | Finer | |
| 6,875,183 B2 | 4/2005 | Cervi | |
| 7,517,322 B2 | 4/2009 | Weikel, Jr. et al. | |
| 7,722,550 B2 | 5/2010 | McClellan | |
| 8,002,811 B2 | 8/2011 | Corradi et al. | |
| 8,029,470 B2 | 10/2011 | Whiting et al. | |
| 8,088,081 B2 | 1/2012 | Field et al. | |
| 8,226,575 B2 | 7/2012 | Levy | |
| 8,876,792 B2 | 11/2014 | Holmin et al. | |
| 9,204,867 B2 | 12/2015 | Peliks | |
| 9,237,883 B2 | 1/2016 | Sundheimer et al. | |
| 9,283,040 B2 | 3/2016 | Hendrick et al. | |
| 9,456,872 B2 | 10/2016 | Hendrick et al. | |
| 9,675,338 B2 | 6/2017 | Shanley et al. | |
| 2003/0023285 A1 | 1/2003 | Eggers et al. | |
| 2005/0124914 A1 * | 6/2005 | Dicarlo | A61B 10/0275 |
| | | | 606/167 |
| 2006/0020286 A1 | 1/2006 | Niermann | |
| 2007/0016101 A1 * | 1/2007 | Feldman | A61B 10/0275 |
| | | | 600/564 |
| 2007/0282344 A1 * | 12/2007 | Yedlicka | A61B 17/1671 |
| | | | 606/80 |
| 2010/0312140 A1 | 12/2010 | Smith et al. | |
| 2011/0313316 A1 * | 12/2011 | Ranpura | A61B 10/0275 |
| | | | 600/566 |
| 2012/0226192 A1 | 9/2012 | Mc Clellan | |
| 2012/0265097 A1 | 10/2012 | Melchiorri et al. | |
| 2014/0171825 A1 * | 6/2014 | Eller | A61B 10/0233 |
| | | | 600/562 |
| 2016/0317133 A1 * | 11/2016 | Orts | A61B 10/0096 |
| 2019/0290312 A1 * | 9/2019 | Herrin | A61B 17/320758 |

* cited by examiner

DEVICES AND METHODS FOR OBTAINING ADENOMYOSIS AND OTHER BIOPSY SAMPLES

BACKGROUND

Technical Field

The present disclosure relates generally to surgical devices and methods. More particularly, the present disclosure relates to devices and methods for obtaining adenomyosis and other biopsy samples.

Background of Related Art

Tissue biopsy is a medical procedure used to obtain a tissue sample from an area of the body. The obtained tissue sample may be tested to assist in diagnosing a medical condition or to assess the effectiveness of a particular treatment.

Adenomyosis is a condition in which the inner lining of the uterus, the endometrial tissue, grows into the uterine wall, causing bleeding, cramping, pain, and other complications. Presently, the diagnosis of adenomyosis is difficult because there is no definitive test for diagnosing adenomyosis; complicating matters further, symptoms of adenomyosis are similar to those of other conditions.

SUMMARY

As used herein, the term "distal" refers to the portion that is described which is farther from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is a tissue biopsy device including an input configured to receive a rotational input and to rotate in a first direction in response thereto, an outer tube, an inner cutting member extending through the outer tube, and a gear assembly coupling one of the outer tube or the inner cutting member with the input such that rotation of the input in the first direction drives rotation of the one of the outer tube or the inner cutting member in the first direction. The gear assembly further couples the other of the outer tube or the inner cutting member with the input such that rotation of the input in the first direction drives rotation of the other of the outer tube or the inner cutting member in a second, opposite direction.

In an aspect of the present disclosure, the input is further configured to translate distally and at least one of the outer tube or the inner cutting member is coupled to the input in fixed longitudinal position such that translation of the input drives translation of the at least one of the outer tube or the inner cutting member.

In another aspect of the present disclosure, the tissue cutting member includes a proximal support and a spiral-shaped distal portion extending distally from the proximal support.

In still another aspect of the present disclosure, the device further includes a handle housing supporting a drive assembly therein. In such aspects, the drive assembly may be configured to connect to the inner drive assembly and to provide the rotational input thereto. More specifically, in aspects, the drive assembly includes a motor configured to provide the rotational input. Alternatively, a manual actuator coupled to the drive assembly actuates the drive assembly to provide the rotational input.

In still another aspect of the present disclosure, the gear assembly includes a sun gear, a plurality of planetary gears disposed about the sun gear in meshed engagement therewith, and a ring gear disposed about the plurality of planetary gears in meshed engagement therewith.

In yet another aspect of the present disclosure, the inner cutting member is coupled to the input such that rotation of the input in the first direction drives rotation of the inner cutting member in the first direction. Further, the sun gear is engaged with the inner cutting member and the outer tube is coupled to the ring gear such that, upon rotation of the inner cutting member in the first direction, the outer tube is rotated in the second, opposite direction.

In still yet another aspect of the present disclosure, the outer tube is coupled to the input such that rotation of the input in the first direction drives rotation of the outer tube in the first direction. In such aspects, the ring gear is engaged with the outer tube and the sun gear is engaged with the inner cutting member such that, upon rotation of the outer tube in the first direction, the inner cutting member is rotated in the second, opposite direction.

In another aspect of the present disclosure, the gear assembly includes a first gear set and a second gear set. The first gear set is directly coupled with the input and the second gear set is coupled with the first gear set. The first and second gear sets are configured to cooperate to reverse the first direction of rotation such that the other of the outer tube or the inner cutting member is rotated in the second, opposite direction.

In still another aspect of the present disclosure, the input is further configured to translate in response to receiving the rotational input. In such aspects, the input may include a helical groove along at least a portion of a length thereof. A drive coupler is at least partially engaged within the helical groove such that the input is translated longitudinally in response to rotation of the input. Additionally, the translation of the input may be imparted to at least one of the inner cutting member or the outer tube.

A method of obtaining a tissue biopsy in accordance with the present disclosure includes positioning a tissue biopsy device adjacent a tissue area of interest. The tissue biopsy device includes an outer tube and an inner cutting member extending through the outer tube. The method further includes driving rotation of the inner cutting member and outer tube in opposite directions to engage tissue with the inner cutting member and cut the engaged tissue with the outer tube to obtain a cylindrical-shaped tissue sample.

In an aspect of the present disclosure, the method further includes driving translation of at least one of the inner cutting member or the outer tube. In aspects, the translation is simultaneous with the rotation.

In another aspect of the present disclosure, the inner cutting member includes a spiral-shaped distal end portion and wherein driving rotation of the inner cutting member includes screwing the spiral-shaped distal end portion into tissue to engage tissue.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Aspects and features of the present disclosure are described in detail with reference to the drawings, in which like reference numerals designate identical or corresponding elements in each of the several views. In the following description, well-known functions or constructions are not described in detail to avoid obscuring the present disclosure in unnecessary detail.

The devices, systems, and methods of the present disclosure may be used for obtaining a tissue sample during any open, minimally invasive, natural orifice, or other surgical procedure. That is, although the devices and methods of the present disclosure are described below with reference to an adenomyosis biopsy procedure, the systems and methods of the present disclosure may also be used for other suitable tissue biopsy procedures.

Figure 1:
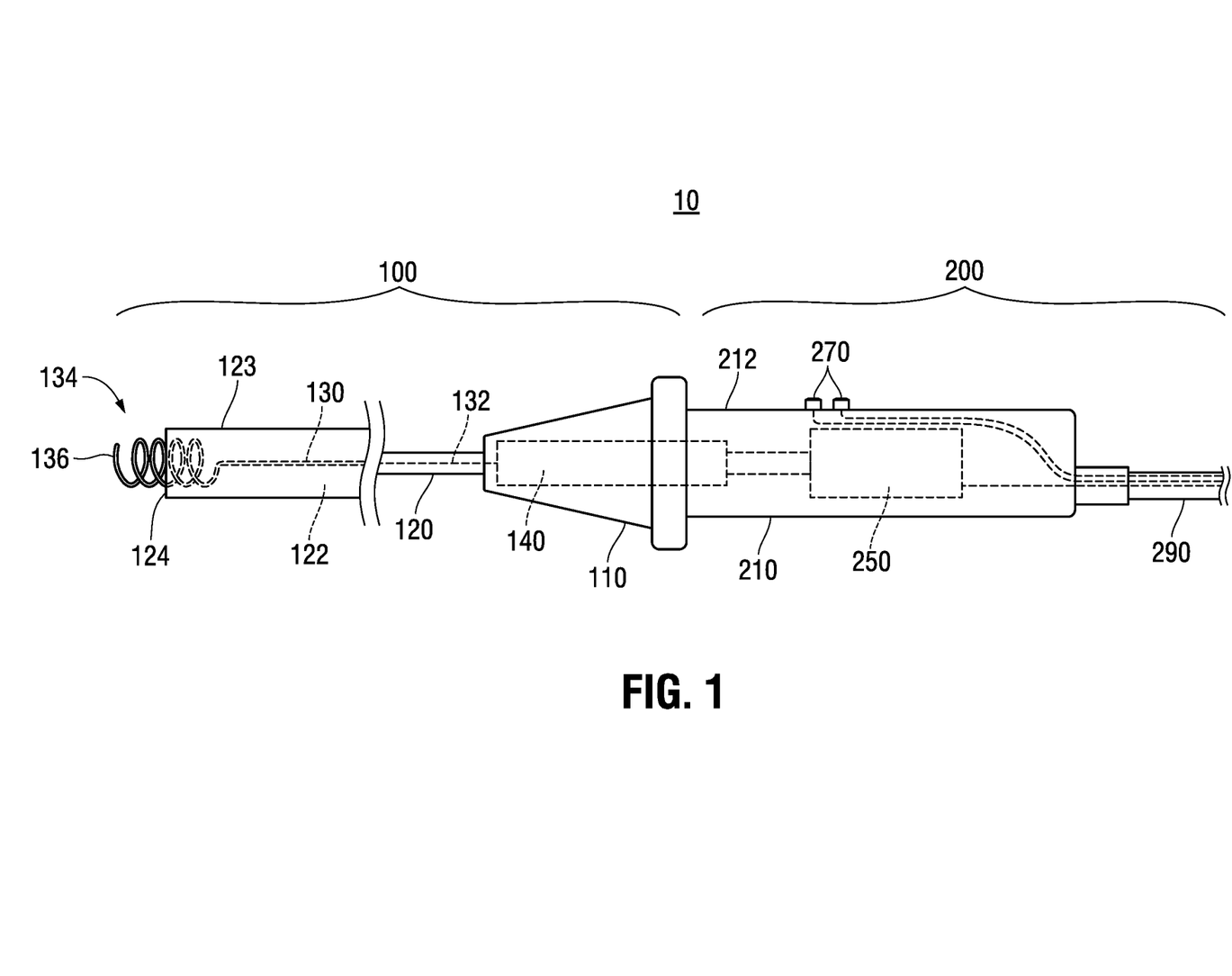
FIG. 1 is a side view of a powered tissue biopsy device provided in accordance with the present disclosure.

With reference to FIG. 1, a device for obtaining adenomyosis and other biopsy samples is shown generally identified by reference numeral 10 including an end effector assembly 100 and a handpiece assembly 200. Handpiece assembly 200 generally includes handle housing 210, a motor 250 disposed within handle housing 210, one or more controls 270, e.g., buttons, disposed on handle housing 210 to facilitate activation of device 10, and a cable 290 enabling connection of handpiece assembly 200 to a power source (not shown) or control console including a power source (not shown), although it is also contemplated that handpiece assembly 200 be configured as a battery-powered device, e.g., including a battery and control electronics within handle housing 210.

Handle housing 210 defines a pencil-grip configuration, although other configurations are also contemplated, e.g., pistol-grip configurations, and includes a distal end portion 212 configured to enable operable engagement of end effector assembly 100 with handpiece assembly 200 such that, upon engagement of end effector assembly 100 with handpiece assembly 200, a portion of end effector assembly 100 extends through distal end portion 212 and into handle housing 210 to couple with motor 250.

With continued reference to FIG. 1, device 10 may be configured as a single-use instrument that is discarded after use or sent to a manufacturer for reprocessing, a reusable instrument capable of being cleaned and/or sterilized for repeated use by the end-user, or a partially-single-use, partially-reusable instrument. With respect to partially-single-use, partially-reusable configurations, handpiece assembly 200 may be configured as a cleanable/sterilizable, reusable component, while end effector assembly 100 is configured as a single-use, disposable/reprocessable component, or vice versa. In any of the above configurations, end effector assembly 100 may be configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies 100 with handpiece assembly 200. In other embodiments, end effector assembly 100 is permanently secured to handpiece assembly 200.

End effector assembly 100 includes a proximal hub housing 110 configured to engage handpiece assembly 200, an outer tube 120 extending distally from proximal hub housing 110, and an inner cutting member 130 disposed within and extending through outer tube 120. Outer tube 120 defines a lumen 122 extending therethrough and a distal edge 124 surrounding an open distal end 123 of outer tube 120. Distal edge 124 may define a sharpened configuration about at least a portion of the circumference thereof, one or more angles, one or more chamfers, cutting teeth disposed about at least a portion of the circumference thereof, and/or any other suitable features configured to facilitate cutting of tissue upon rotation of distal edge 124 (as a result of rotation of outer tube 120) relative to tissue.

Inner cutting member 130, as noted above, is disposed within and extends through outer tube 120. Inner cutting member 130 includes a proximal support 132 formed as a wire, rod, tube, or in any other suitable manner. Inner cutting member 130 further includes a spiral-shaped distal portion 134 extending distally from proximal support 132. In some configurations, proximal support and spiral-shaped distal portion 134 are integrally formed as a single component, e.g., a continuous piece of wire. Spiral-shaped distal portion 134 may define a sharpened free end 136 or any other suitable configuration of free distal end 136. Spiral-shaped distal portion 134, lead by free distal end 136, is configured to engage and bore into tissue upon rotation of inner cutting member 130 relative thereto, e.g., in a corkscrew-like fashion, in a direction of the spiral of spiral-shaped distal portion 136. On the other hand, spiral-shaped distal portion 134 may be withdrawn from tissue via rotation in the opposite direction, e.g., opposite the direction of the spiral of spiral-shaped distal portion 136.

Inner cutting member 130 may extend to the distal end of outer tube 120 such that free distal end 136 of spiral-shaped distal portion 134 is disposed adjacent distal edge 124 of outer tube 120; may extend distally beyond the distal end of outer tube 120 such that at least a portion of spiral-shaped distal portion 134 extends distally from the distal end of outer tube 120; or may be recessed within outer tube 120 such that free distal end 136 of spiral-shaped distal portion 134 is disposed within lumen 122 of outer tube 120 and proximally-spaced from distal edge 124 of outer tube 120. Further, inner cutting member 130 may be longitudinally fixed relative to outer tube 120 (and/or proximal hub housing 110), or may be configured to translate longitudinally relative to outer tube 120 (and/or proximal hub housing 110). Alternatively or additionally, outer tube 120 may be configured to translate longitudinally relative to inner cutting member 130 (and/or proximal hub housing 110). Relative translation between inner cutting member 130 and outer tube 120 may be effected to facilitate capturing a biopsy sample, withdrawal of device 10 (and the biopsy sample) from tissue, and/or removal of the biopsy sample from device 10 after capture and withdrawal.

End effector assembly 100 further includes an inner drive assembly 140 at least partially disposed within proximal hub housing 110 and coupled to outer tube 120 and inner cutting member 130. Inner drive assembly 140, more specifically, is configured to couple motor 250 of handpiece assembly 200 with both outer tube 120 and inner cutting member 130 such that, upon activation of motor 250 (which provides a rotational output, although translational outputs or combination rotational and translational outputs are also contemplated), outer tube 120 is driven to rotate in a first direction and inner cutting member 130 is driven to rotate in a second, opposite direction. Inner drive assembly 140 may further be configured, in embodiments, to drive translation of outer tube 120 and/or inner cutting member 130 in concert, oppositely, alternatingly, or in any other suitable manner. Various embodiments of inner drive assemblies 140 suitable for use with device 10 are detailed below with reference to FIGS. 3-6.

Figure 2:
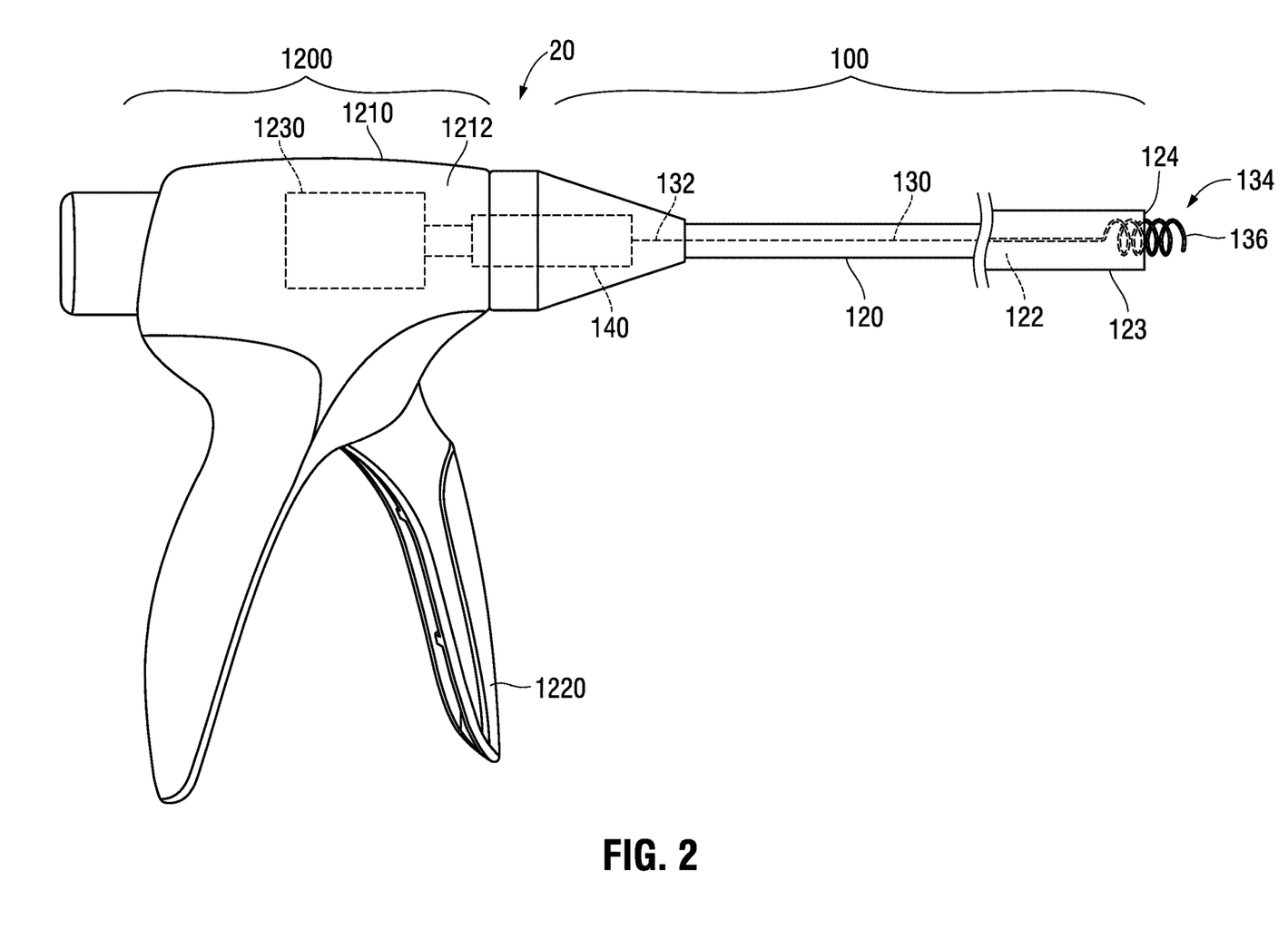
FIG. 2 is a side view of a manual tissue biopsy device provided in accordance with the present disclosure.

Turning to FIG. 2, another device for obtaining adenomyosis and other biopsy samples is shown generally identified by reference numeral 20 including end effector assembly 100 and a handpiece assembly 1200.

Handpiece assembly 1200 is configured for manual actuation and generally includes a handle housing 1210, a trigger 1220 pivotably coupled to handle housing 1210, and a drive assembly 1230 disposed within handle housing 1210 and coupled to trigger 1220. Handle housing 1210 defines a pistol-grip configuration, although other configurations are also contemplated; further, rather than providing a pivoting trigger 1220 to actuate handpiece assembly 1200, handpiece assembly 1200 may include one or more slidable plungers, buttons, etc. A distal end portion 1212 of handle housing 1210 is configured to enable operable engagement of end effector assembly 100 with handpiece assembly 1200 such that, upon engagement of end effector assembly 100 with handpiece assembly 1200, a portion of end effector assembly 100 extends through distal end portion 1212 and into handle housing 1210 to couple with drive assembly 1230.

With continued reference to FIG. 2, device 20 may be configured as a single-use instrument that is discarded after use or sent to a manufacturer for reprocessing, a reusable instrument capable of being cleaned and/or sterilized for repeated use by the end-user, or a partially-single-use, partially-reusable instrument. With respect to partially-single-use, partially-reusable configurations, handpiece assembly 1200 may be configured as a cleanable/sterilizable, reusable component, while end effector assembly 100 is configured as a single-use, disposable/reprocessable component, or vice versa. In any of the above configurations, end effector assembly 100 may be configured to releasably engage handpiece assembly 1200 to facilitate disposal/reprocessing of any single-use components and cleaning and/or sterilization of any reusable components. Further, enabling releasable engagement of end effector assembly 100 with handpiece assembly 1200 allows for use of different end effector assemblies 100 with handpiece assembly 1200. In other embodiments, end effector assembly 100 is permanently secured to handpiece assembly 1200.

End effector assembly 100 is detailed above with respect to device 10 (FIG. 1) and, thus, the description thereof is not repeated with respect to device 20 except as necessary to detail the use of end effector assembly 100 with handpiece assembly 1200.

Drive assembly 1230 of handpiece assembly 1200 is configured and coupled to trigger 1220 such that actuation of trigger 1220, e.g., pivoting of trigger 1220 relative to handle housing 1210, actuates drive assembly 1230 to provide a rotational output, although in embodiments, translational outputs and/or combination rotational and translational outputs are also contemplated. Inner drive assembly 140 of end effector assembly 100 is configured to couple drive assembly 1230 of handpiece assembly 1200 with both outer tube 120 and inner cutting member 130 such that, upon activation of drive assembly 1230, e.g., in response to actuation of trigger 1220, outer tube 120 is driven to rotate in a first direction and inner cutting member 130 is driven to rotate in a second, opposite direction. Inner drive assembly 140 may further be configured, in embodiments, to drive translation of outer tube 120 and/or inner cutting member 130 in concert, oppositely, alternatingly, or in any other suitable manner. Various embodiments of inner drive assemblies 140 suitable for use with device 10 are detailed below with reference to FIGS. 3-6.

Figure 3:
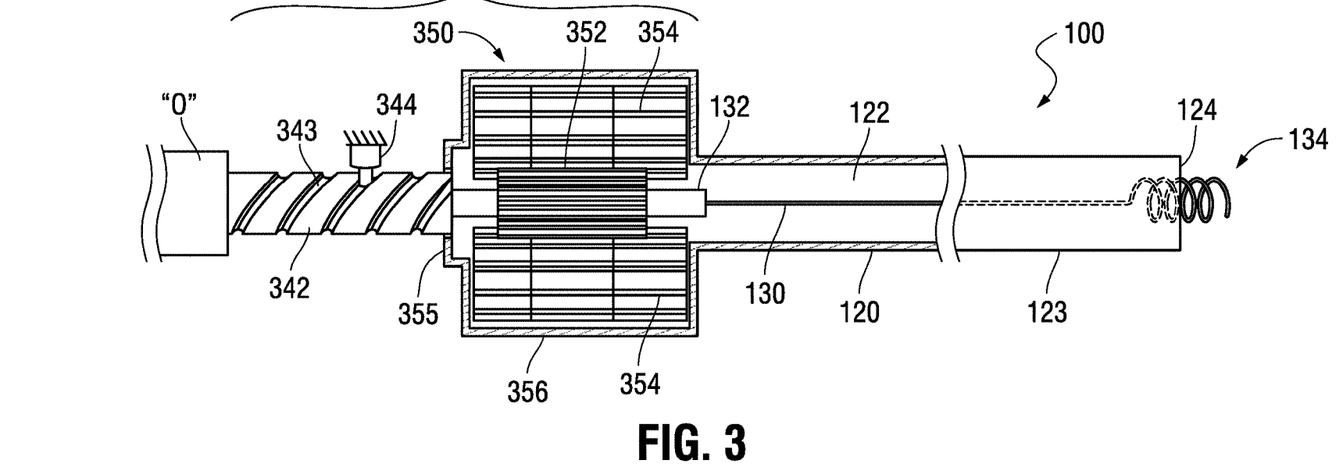
FIG. 3 is a side, partial cross-sectional view of an inner drive assembly and end effector assembly configured for use with the device of FIG. 1, the device of FIG. 2, or any other suitable tissue biopsy device.

Turning to FIG. 3, an inner drive assembly configured for use with end effector assembly 100 is shown generally identified by reference numeral 340. Inner drive assembly 340 includes a proximal driver 342, a drive coupler 344, and a gear assembly 350. Proximal driver 342 is coupled to and configured to receive a rotational driving force from a rotational output "O," e.g., the rotational output of motor 250 (FIG. 1), the rotational output of drive assembly 1230 (FIG. 2), or any other suitable rotational output "O," although translational outputs and/or combination rotational and translational outputs are also contemplated. The rotational output "O" drives rotation of proximal driver 342. Proximal driver 342 defines a helical groove 343 extending along at least a portion of a length thereof. Helical groove 343 may define a constant or variable pitch, and may be a single helix or a double helix for uni-directional or reciprocal motion, respectively. With respect to a double helix, the ends may be blended to enable transition from one translational direction to the other. Drive coupler 344 is substantially fixed and is at least partially disposed within helical groove 343. In this manner, rotational driving of proximal driver 342 also results in translation of proximal driver 342 as drive coupler 344 travels through helical groove 343. Proximal driver 342 is engaged, directly or indirectly, with a proximal end portion of proximal support 132 of inner cutting member 130 such that rotation and translation of proximal driver 342 affects similar rotation and translation of inner cutting member 130. However, it is also contemplated that gearing or other suitable coupling features be provided between proximal driver 342 and proximal support 132 to amplify or attenuate the rotation and/or translation of inner cutting member 130 relative to that of proximal driver 342.

Gear assembly 350 of inner drive assembly 340 includes a sun gear 352 fixedly engaged about proximal support 132 of inner cutting member 130, a plurality of planetary gears 354 disposed in meshed engagement with and disposed radially about sun gear 352 in fixed orbital position relative thereto (e.g., via a carrier 355), and a ring gear 356 disposed about the plurality of planetary gears 354 in meshed engagement with each of the planetary gears 354. Thus, rotation of sun gear 352, e.g., in response to rotation of proximal support 132 of inner cutting member 130 as driven by proximal driver 342, rotates the plurality of planetary gears 354 to, in turn, rotate ring gear 356. Carrier 355 inhibits orbiting of planetary gears 354 while permitting rotation thereof such that rotation of sun gear 352 is imparted to ring gear 356 via planetary gears 354. More specifically, rotation of sun gear 352 in a first direction results in rotation of ring gear 356 in a second, opposite direction.

Continuing with reference to FIG. 3, ring gear 356 is engaged, directly or indirectly, with a proximal end portion of outer tube 120 such that rotation of ring gear 356 affects similar rotation of outer tube 120. Thus, with proximal driver 342 driving rotation of inner cutting member 130 in a first direction, and carrier 355 inhibiting orbiting of planetary gears 354, ring gear 356 is rotated to drive rotation of outer tube 120 in the second, opposite direction.

In addition to rotation, as noted above, the engagement of drive coupler 344 within helical groove 343 drives translation of proximal driver 342 which, in turn, is imparted to inner cutting member 130 and sun gear 352 (which is engaged about inner cutting member 130). Planetary gears 354 may define elongated configurations, enabling sun gear 352 to translate relative thereto while maintaining mesh engagement therebetween. In such configurations, inner cutting member 130 is driven to rotate in the first direction and is also driven to translate, while outer tube 120 is driven to rotate in the second, opposite direction while remaining translationally fixed.

Alternatively, planetary gears 354 and ring gear 356 may be translationally fixed relative to sun gear 352 such that translation of sun gear 352 affects similar translation of planetary gears 354 and ring gear 356. In such configurations, inner cutting member 130 is driven to rotate in the first direction and is also driven to translate, while outer tube 120 is driven to rotate in the second, opposite direction and is translated similarly as inner cutting member 130. The translational fixing may be provided by translationally fixing carrier 355 and/or ring gear 356 to proximal driver 342, for example, or in any other suitable manner.

Figure 4:
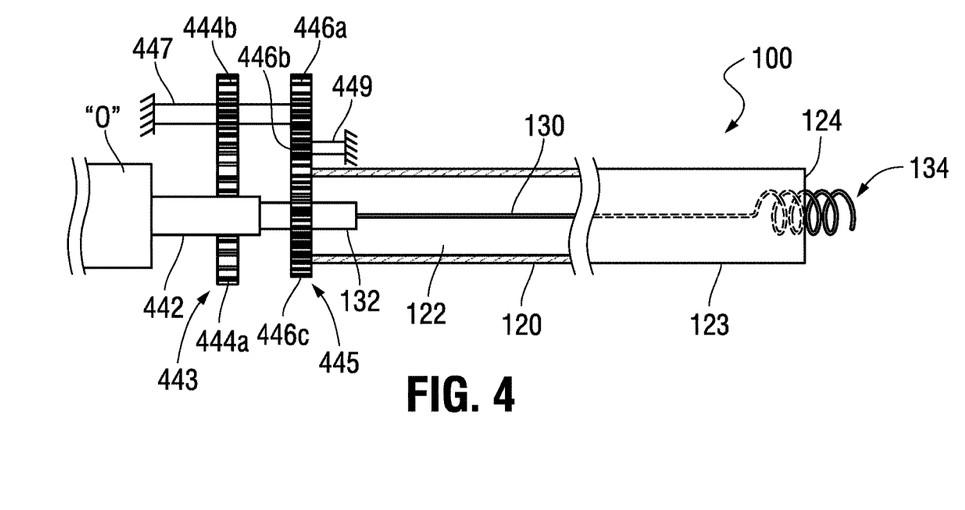
FIG. 4 is a side, partial cross-sectional view of another inner drive assembly and end effector assembly configured for use with the device of FIG. 1, the device of FIG. 2, or any other suitable tissue biopsy device.

With reference to FIG. 4, another inner drive assembly configured for use with end effector assembly 100 is shown generally identified by reference numeral 440. Inner drive assembly 440 includes an input shaft 442, a first set of gears 443 including gears 444a, 444b, a second set of gears 445 including gears 446a, 446b, 446c, and first and second gear shafts 447, 449. Input shaft 442 is coupled to and configured to receive a rotational driving force from a rotational output "O," e.g., the rotational output of motor 250 (FIG. 1), the rotational output of drive assembly 1230 (FIG. 2), or any other suitable rotational output "O," although translational outputs and/or combination rotational and translational outputs are also contemplated. The rotational output "O" drives rotation of input shaft 442. Input shaft 442 is engaged, directly or indirectly, with a proximal end portion of proximal support 132 of inner cutting member 130 such that rotation and translation of input shaft 442 affects similar rotation and translation of inner cutting member 130. However, it is also contemplated that gearing or other suitable coupling features be provided between input shaft 442 and proximal support 132 to amplify or attenuate the rotation of inner cutting member 130 relative to that of input shaft 442.

First set of gears 443 includes first gear 444a engaged about input shaft 442 such that rotation of input shaft 442 similarly rotates first gear 444a. First set of gears 443 further includes second gear 444b engaged about first gear shaft 447 and disposed in meshed engagement with first gear 444a. In this manner, rotation of first gear 444a, e.g., in response to rotation of input shaft 442 provided by rotational output "O," rotates second gear 444b and, thus, first gear shaft 447. The rotations of first gear 444a and second gear 444b are in opposite directions.

First gear shaft 447 also supports third gear 446a of the second set of gears 445 thereon. Third gear 446a is disposed in meshed engagement with fourth gear 446b of the second set of gears 445, which is supported on second gear shaft 449. Fourth gear 446b, in turn, is disposed in meshed engagement with fifth gear 446c of the second set of gears 445. Fifth gear 446c is fixedly engaged (directly or indirectly) with a proximal end portion of outer tube 120. As a result of the above-detailed configuration, rotation of first gear shaft 447 drives rotation of third gear 446a, fourth gear 446b, and fifth gear 446c to thereby drive rotation of outer tube 120 in a second, opposite direction. More specifically, as noted above, rotation of first gear 444a in the first direction, e.g., in response to rotation of input shaft 442 provided by rotational output "O," rotates second gear 444b and first gear shaft 447 in the second, opposite direction. This rotation of first gear shaft 447 affects rotation of outer tube 120 in the second, opposite direction (whereby third gear 446a rotates in the second, opposite direction to rotate fourth gear 446b in the first direction to, in turn, rotate fifth gear 446c in the second, opposite direction). Accordingly, inner cutting member 130 is driven to rotate in the first direction, while outer tube 120 is driven to rotate in the second, opposite direction.

Figure 5:
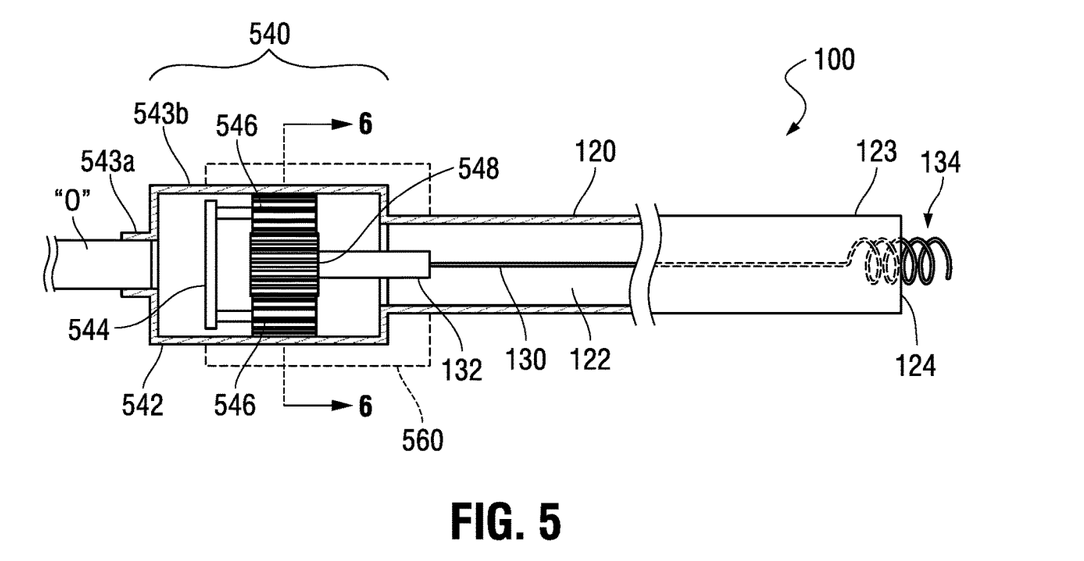
FIG. 5 is a side, partial cross-sectional view of yet another inner drive assembly and end effector assembly configured for use with the device of FIG. 1, the device of FIG. 2, or any other suitable tissue biopsy device.
Figure 6:
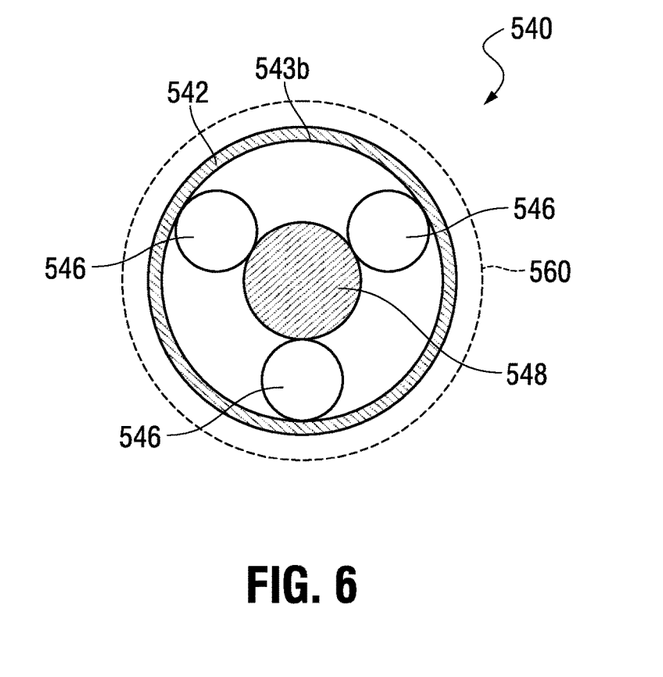
FIG. 6 is a transverse, cross-sectional view taken across section line "6-6" of FIG. 5.

Referring to FIGS. 5 and 6, still another inner drive assembly configured for use with end effector assembly 100 is shown generally identified by reference numeral 540. Inner drive assembly 540 includes a driver housing 542, a carrier 544, a plurality of planetary gears 546, and a sun gear 548. Driver housing 542 includes an input 543a coupled to and configured to receive a rotational driving force from a rotational output "O," e.g., the rotational output of motor 250 (FIG. 1), the rotational output of drive assembly 1230 (FIG. 2), or any other suitable rotational output "O," although translational outputs and/or combination rotational and translational outputs are also contemplated. The rotational output "O" drives rotation of driver housing 542. Driver housing 542 defines a ring gear 543b on an interior surface thereof and is engaged, directly or indirectly, with a proximal end portion of outer tube 120 such that rotation of driver housing 542, e.g., in response to receiving the rotational output "O," drives similar rotation of outer tube 120.

Carrier 544 rotatably supports the plurality of planetary gears 546 within driver housing 542 to inhibit orbiting of planetary gears 546 about sun gear 548 while permitting rotation thereof. Planetary gears 546, more specifically, are disposed within driver housing 542 in meshed engagement with ring gear 543b of driver housing 542. Planetary gears 546 are also disposed in meshed engagement with and disposed radially about sun gear 548 in fixed orbital position relative thereto (via carrier 544). Thus, rotation of ring gear 543b of driver housing 542 rotates the plurality of planetary gears 546 to, in turn, rotate sun gear 548. Sun gear 548 is engaged about a proximal end portion of proximal support 132 of inner cutting member 130 such that rotation of sun gear 548 drives rotation of inner cutting member 130. In the above-detailed configuration, outer tube 120 is driven to rotate in the first direction (as provided by rotational output "O"), while inner cutting member 130 is driven to rotate in the second, opposite direction.

As an alternative to driver housing 542 coupling with rotational output "O," inner drive assembly 540 along with outer tube 120 and inner cutting member 130 may be a stand-alone device wherein the rotational input it provided by manual rotation of driver housing 542 (or other suitable actuator associated therewith). In such configurations, an outer collar 560 (illustrated in phantom in FIGS. 5 and 6) may be provided for grasping, to facilitate rotation of driver housing 542 relative thereto. Outer collar 560 and carrier 544 may be fixedly engaged with one another, directly or indirectly.

Figure 7A:
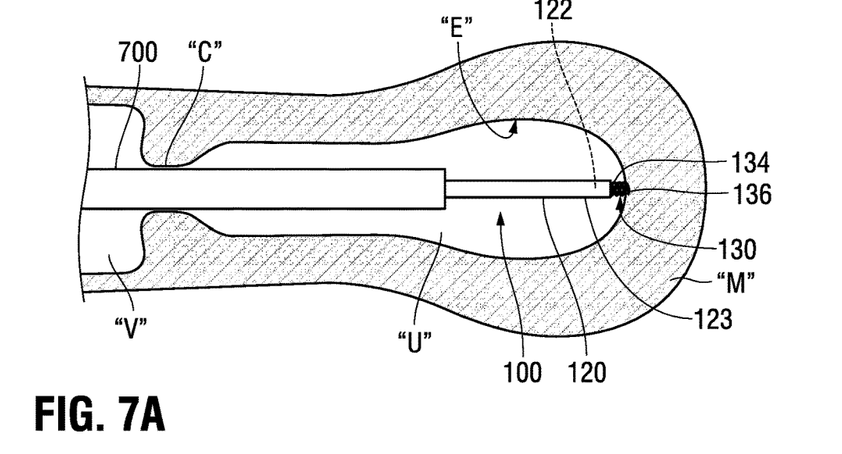
FIGS. 7A-7C are longitudinal, cross-sectional views progressively illustrating obtaining an adenomyosis biopsy sample in accordance with the present disclosure.
Figure 7B:
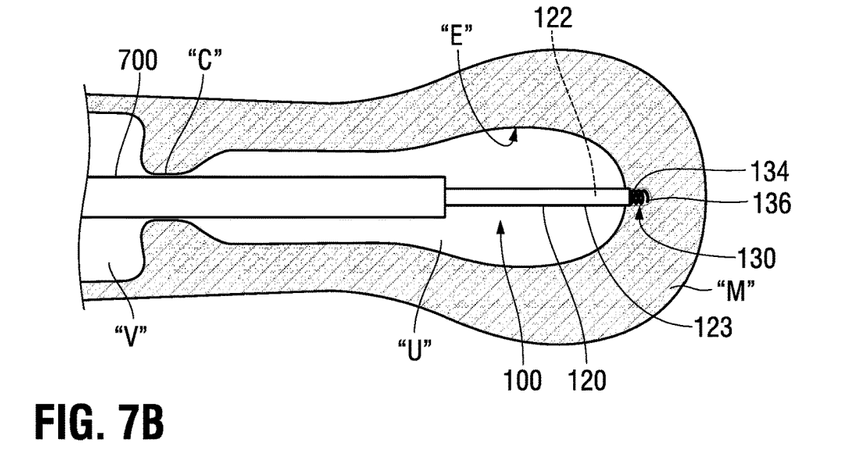
Figure 7C:
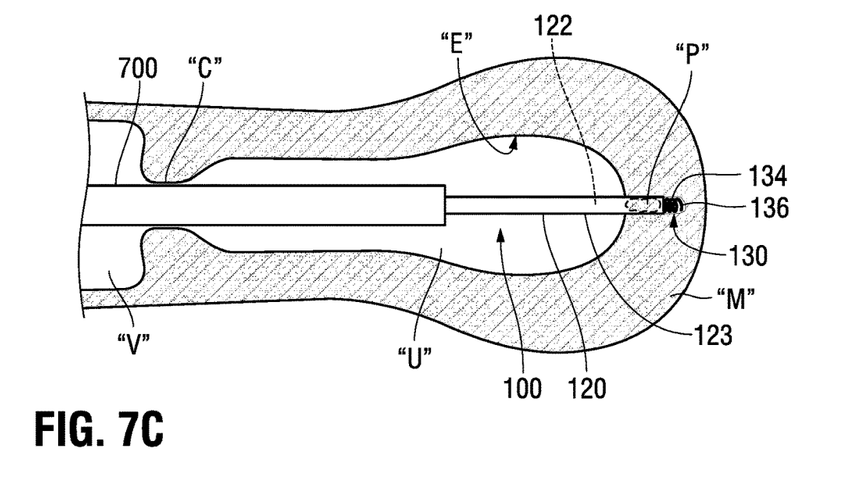

Turning to FIGS. 7A-7C, use of end effector assembly 100 of the present disclosure (whether used with device 10 (FIG. 1), device 20 (FIG. 2), or any other suitable device; whether incorporating inner drive assembly 340 (FIG. 3), inner drive assembly 440 (FIG. 4), or inner drive assembly 540 (FIGS. 5 and 6)) to obtain an adenomyosis biopsy sample is described. Initially, with reference to FIG. 7A, a hysteroscope 700 or other suitable access device may be inserted transvaginally through the vagina "V," the cervix "C," and into the uterus "U." End effector assembly 100, led by the distal end thereof, may then be inserted through a working channel of hysteroscope 700 and into the uterus "U" and manipulated into position such that free distal end 136 of spiral-shaped distal portion 134 of inner cutting member 130 and/or distal end 123 of outer tube 120 are positioned adjacent an area of interest, e.g., adjacent or in contact with endometrial tissue "E."

Referring to FIGS. 7A and 7B, once the above-noted position has been achieved, end effector assembly 100 is activated e.g., to drive the inner drive assembly thereof (for example, inner drive assembly 340 (FIG. 3), inner drive assembly 440 (FIG. 4), or inner drive assembly 540 (FIGS. 5 and 6)), such that spiral-shaped distal portion 134 of inner cutting member 130, led by free distal end 136 thereof, is rotationally driven and is either translationally driven or the entirety of end effector assembly 100 is translated. Either way, spiral-shaped distal portion 134 is driven through the endometrial tissue "E" and into the myometrial tissue "M." The spiral-shaped distal portion 134 functions as an anchor to bore into, grasp, and retain the myometrial tissue "M."

With additional reference to FIG. 7C, before, simultaneously with, after, or in overlapping temporal relation with the activation of inner cutting member 130, outer tube 120 is activated such that outer tube 120, lead by distal edge 124, is rotationally driven and is either translationally driven or the entirety of end effector assembly 100 is translated such that outer tube 120 is advanced through the endometrial tissue "E" and into the myometrial tissue "M," cutting out a cylindrical plug of tissue "P" that is retained within lumen 122 of outer tube 120. The opposite rotations of inner cutting member 130 and outer tube 120 facilitates retention and cutting of tissue, thereby facilitating obtaining a biopsy sample, the plug of tissue "P."

Once a sufficient bite of tissue is obtained, end effector assembly 100 may be withdrawn from the surgical site and the obtained biopsy sample, the plug of tissue "P," may be removed from end effector assembly 100 for analysis.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A tissue biopsy device, comprising:
    an input drive shaft configured to receive a rotational input, where, in response to the rotational input, the input drive shaft is configured to rotate in a first direction and translate longitudinally;
    an outer tube;
    an inner cutting member extending through the outer tube; and
    a gear assembly coupling one of the outer tube or the inner cutting member with the input drive shaft such that rotation of the input drive shaft in the first direction drives rotation of the one of the outer tube or the inner cutting member in the first direction, and coupling the other of the outer tube or the inner cutting member with the input drive shaft such that rotation of the input drive shaft in the first direction drives rotation of the other of the outer tube or the inner cutting member in a second, opposite direction,
    wherein longitudinal translation of the input drive shaft drives longitudinal translation of at least one of the outer tube or the inner cutting member relative to another of the outer tube or the inner cutting member.

2. The tissue biopsy device according to claim 1, wherein the inner cutting member includes a proximal support and a spiral-shaped distal portion extending distally from the proximal support.

3. The tissue biopsy device according to claim 1, further comprising a handle housing supporting an actuator, the actuator configured to connect to the input drive shaft and to provide the rotational input to the input drive shaft.

4. The tissue biopsy device according to claim 3, wherein the actuator includes a motor configured to provide the rotational input.

5. The tissue biopsy device according to claim 3, wherein the actuator includes a manual actuator coupled to the drive assembly such that, in response to actuation of the manual actuator, the actuator provides the rotational input.

6. The tissue biopsy device according to claim 1, wherein the gear assembly includes a sun gear, a plurality of planetary gears disposed about the sun gear in meshed engagement with the sun gear, and a ring gear disposed about the plurality of planetary gears in meshed engagement with the plurality of planetary gears.

7. The tissue biopsy device according to claim 6, wherein the inner cutting member is coupled to the input drive shaft such that rotation of the input drive shaft in the first direction drives rotation of the inner cutting member in the first direction, wherein the sun gear is engaged with the inner cutting member, and wherein the outer tube is coupled to the ring gear such that, upon rotation of the inner cutting member in the first direction, the outer tube is rotated in the second, opposite direction.

8. The tissue biopsy device according to claim 6, wherein the outer tube is coupled to the input drive shaft such that rotation of the input drive shaft in the first direction drives rotation of the outer tube in the first direction, wherein the ring gear is engaged with the outer tube, and wherein the sun gear is engaged with the inner cutting member such that, upon rotation of the outer tube in the first direction, the inner cutting member is rotated in the second, opposite direction.

9. The tissue biopsy device according to claim 1, wherein the gear assembly includes a first gear set and a second gear set, the first gear set directly coupled with the input drive shaft and the second gear set coupled with the first gear set, wherein the other of the outer tube or the inner cutting member is coupled with the second gear set, and wherein the first and second gear sets are configured to cooperate to reverse the first direction of rotation such that the other of the outer tube or the inner cutting member is rotated in the second, opposite direction.

10. The tissue biopsy device according to claim 1, wherein the input drive shaft includes a helical groove along at least a portion of a length thereof, and wherein a drive coupler is at least partially engaged within the helical groove such that the input drive shaft is translated longitudinally in response to rotation of the input.

11. A method of obtaining a tissue biopsy, the method comprising:
 driving an input drive shaft of a tissue biopsy device having an outer tube and an inner cutting member extending through the outer tube in a first direction to rotate the inner cutting member and outer tube in opposite directions to engage tissue with the inner cutting member and cut the engaged tissue with the outer tube to obtain a cylindrical-shaped tissue sample; wherein driving the input drive shaft includes a gear assembly coupling one of the outer tube or the inner cutting member with the input drive shaft such that rotation of the input drive shaft in the first direction drives rotation of the one of the outer tube or the inner cutting member in the first direction, and coupling the other of the outer tube or the inner cutting member with the input drive shaft such that rotation of the input drive shaft in the first direction drives rotation of the other of the outer tube or the inner cutting member in a second, opposite direction,
 wherein rotation of the input drive shaft longitudinally translates at least one of the inner cutting member or the outer tube to capture the cylindrical-shaped tissue sample.

12. The method according to claim 11, wherein the translation is simultaneous with the rotation.

13. The method according to claim 11, wherein the inner cutting member includes a spiral-shaped distal end portion and wherein driving the input drive shaft in the first direction to rotate the inner cutting member includes screwing the spiral-shaped distal end portion into tissue to engage tissue.

14. A tissue biopsy device, comprising:
 an input drive shaft configured to receive a rotational input, where, in response to the rotational input, the input drive shaft is configured to rotate in a first direction and translate longitudinally;
 an outer tube;
 an inner cutting member extending through the outer tube;
 an actuator configured to connect to the input drive shaft, the actuator providing rotational input to the input drive shaft upon actuation thereof; and
 a gear assembly coupling one of the outer tube or the inner cutting member with the input drive shaft such that rotation of the input drive shaft in the first direction drives rotation of the one of the outer tube or the inner cutting member in the first direction, and coupling the other of the outer tube or the inner cutting member with the input drive shaft such that rotation of the input drive shaft in the first direction drives rotation of the other of the outer tube or the inner cutting member in a second, opposite direction,
 wherein longitudinal translation of the input drive shaft drives longitudinal translation of at least one of the outer tube or the inner cutting member relative to another of the outer tube or the inner cutting member.

* * * * *